United States Patent
Quittman et al.

(10) Patent No.: US 8,242,044 B2
(45) Date of Patent: Aug. 14, 2012

(54) PROCESS AND CATALYST

(75) Inventors: Wilhelm Quittman, Visp (CH); Thomas Peter Belser, Visp (CH); Rhony Niklaus Aufdenblatten, Visp (CH)

(73) Assignee: AstraZeneca AB, Sodertalje (SE)

( * ) Notice: Subject to any disclaimer, the term of this patent is extended or adjusted under 35 U.S.C. 154(b) by 142 days.

(21) Appl. No.: 12/887,623

(22) Filed: Sep. 22, 2010

(65) Prior Publication Data

US 2011/0071290 A1   Mar. 24, 2011

(30) Foreign Application Priority Data

Sep. 23, 2009 (EP) .................................. 09012080

(51) Int. Cl.
*B01J 27/19* (2006.01)
*C07D 239/02* (2006.01)

(52) U.S. Cl. ........................................ 502/211; 544/316
(58) Field of Classification Search .................. 544/316; 502/211

See application file for complete search history.

(56) References Cited

U.S. PATENT DOCUMENTS

| 2,932,626 A | | 4/1960 | Von Fuener et al. |
| 3,953,509 A | * | 4/1976 | Greco .......................... 564/418 |
| 4,020,107 A | | 4/1977 | Kosak |
| 4,375,550 A | | 3/1983 | Bird et al. |

FOREIGN PATENT DOCUMENTS

| EP | 1533029 | 5/2005 |
| WO | 9905143 | 2/1999 |
| WO | 0034283 | 6/2000 |
| WO | 0192263 | 12/2001 |

* cited by examiner

*Primary Examiner* — James O Wilson
*Assistant Examiner* — Ebenezer O Sackey
(74) *Attorney, Agent, or Firm* — Pepper Hamilton LLP

(57) ABSTRACT

Aromatic or heteroaromatic nitro compounds are catalytically hydrogenated to the corresponding amines in the presence of a platinum catalyst comprising elemental platinum on a support; the platinum catalyst is modified with a molybdenum compound and a phosphorus compound wherein the phosphorus has an oxidation state of less than +5, e.g. hypophosphorous acid; the catalyst is particularly useful in the hydrogenation of nitro compounds with halogen and/or sulfur-containing substituents.

14 Claims, No Drawings

PROCESS AND CATALYST

CROSS-REFERENCE TO RELATED APPLICATIONS

This application claims priority under 35 U.S.C. §119(a)-(d) of European Application No. 09012080.9 Sep. 23, 2009, which is incorporated herein by reference in its entirety.

FIELD OF THE INVENTION

The invention relates to a process for the catalytic hydrogenation of aromatic and heteroaromatic nitro compounds to the corresponding amines. It further relates to a modified supported platinum catalyst containing molybdenum and phosphorus.

BACKGROUND OF THE INVENTION

The reduction of aromatic and heteroaromatic nitro compounds provides an important synthetic route to the corresponding amines. However, the reaction proceeds over several intermediates and it is sometimes difficult to achieve a complete reduction. In particular the hydroxylamine intermediate often poses a problem since it is relatively stable and may accumulate in the reaction mixture. When the reduction is carried out via catalytic hydrogenation, other reducible substituents, such as halogen atoms or groups containing carbon-carbon multiple bonds, or sulfur-containing groups (e.g. thioether groups) can cause unwanted side reactions (e.g. hydrogenolysis or hydrogenation of carbon-carbon multiple bonds) or inhibition effects ("catalyst poisoning"), which result in formation of undesired byproducts, unsatisfactory yields, or the requirement of uneconomically large amounts of catalyst. It has been an objective of the present invention to provide a method for the selective reduction of aromatic and heteroaromatic nitro compounds to the corresponding amines that gives good yields even in the presence of halogen or oxygen-containing or sulfur-containing substituents without requiring drastic reaction conditions or unreasonably large amounts of catalyst.

According to the invention, this objective has been achieved by the processes and the catalysts described herein. It has been found that the performance of a supported platinum catalyst in the hydrogenation of an aromatic or heteroaromatic nitro compound to the corresponding amine can be substantially improved by modifying it with a molybdenum compound and a phosphorus compound wherein the phosphorus has an oxidation state of less than +5.

SUMMARY OF THE INVENTION

The present invention provides processes for the catalytic hydrogenation of an aromatic or heteroaromatic nitro compound to the corresponding amine in the presence of a platinum catalyst comprising elemental platinum on a support, characterized in that the platinum catalyst has been modified with a molybdenum compound and a phosphorus compound wherein the phosphorus has an oxidation state of less than +5. In some embodiments, the phosphorus compound is hypophosphorous acid or a salt or reaction product thereof. In any of the above embodiments, the molybdenum compound is an orthomolybdate or reaction product thereof. In any of the above embodiments, the molybdenum compound is ammonium orthomolybdate or zinc orthomolybdate or a reaction product thereof. In any of the above embodiments, the support is charcoal. In any of the above embodiments, the catalyst has a molybdenum/platinum molar ratio of 1:1 to 100:1 and a phosphorus/molybdenum molar ratio of 1:1 to 100:1. In any of the above embodiments, the catalyst has a molybdenum/platinum molar ratio of 1:1 to 10:1 and a phosphorus/molybdenum molar ratio of 1:1 to 10:1. In any of the above embodiments, the aromatic or heteroaromatic nitro compound is substituted with one or more substituents selected from the group consisting of halogen atoms and oxygen-containing or sulfur-containing groups. In any of the above embodiments, the heteroaromatic nitro compound is a nitropyrimidine. In any of the above embodiments, the heteroaromatic nitro compound is a compound of formula (II)

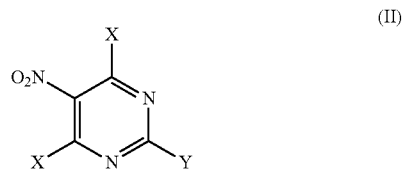

(II)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl. In any of the above embodiments, the heteroaromatic nitro compound is 4,6-dichloro-5-nitro-2-(propylsulfanyl)pyrimidine.

The present invention also provides modified supported platinum catalysts containing molybdenum and a phosphorus compound, wherein the phosphorus has an oxidation state of less than +5, obtainable by treating a supported platinum catalyst with an aqueous solution of hypophosphorous acid or a salt thereof and an orthomolybdate in a molybdenum/platinum molar ratio of 1:1 to 100:1 and a phosphorus/molybdenum molar ratio of 1:1 to 100:1. In some embodiments, the molybdenum/platinum molar ratio is from 1:1 to 10:1 and the phosphorus/molybdenum molar ratio is from 1:1 to 10:1. In any of the above embodiments, the orthomolybdate is selected from ammonium orthomolybdate and zinc orthomolybdate.

DESCRIPTION OF EMBODIMENTS

In particular, the invention provides a process for the catalytic hydrogenation of an aromatic or heteroaromatic nitro compound to the corresponding amine in the presence of a platinum catalyst comprising elemental platinum on a support, characterized in that the platinum catalyst has been modified with a molybdenum compound and a phosphorus compound wherein the phosphorus has an oxidation state of less than +5.

In particular, the phosphorus compound is hypophosphorous acid or a salt or reaction product thereof and the molybdenum compound is an orthomolybdate or reaction product thereof (for example, ammonium orthomolybdate or zinc orthomolybdate or a reaction product thereof).

In particular, the invention provides a process wherein the aromatic or heteroaromatic nitro compound is substituted with one or more substituents selected from the group consisting of halogen atoms and oxygen-containing or sulfur-containing groups; especially the group consisting of halogen atoms and sulfur-containing groups.

In particular, the present invention concerns a process for the preparation of 5-aminopyrimidines which are useful intermediates in the preparation of pharmaceutically active triazolo[4,5-d]pyrimidine cyclopentanes.

The compound [1S-(1α,2α,3β(1S*,2R*),5β)]-3-[7-[2-(3,4-difluorophenyl)-cyclopropyl]amino]-5-(propylthio)-3H-1, 2,3-triazolo[4,5-d]pyrimidin-3-yl)-5-(2-hydroxyethoxy)-cyclopentane-1,2-diol (Compound A), and similar such compounds, are disclosed in WO 00/34283 and WO 99/05143 as pharmaceutically active $P_{2T}$ (which is now usually referred to as $P_2Y_{12}$) receptor antagonists. Such antagonists can be used as, inter alia, inhibitors of platelet activation, aggregation or degranulation.

Compound A

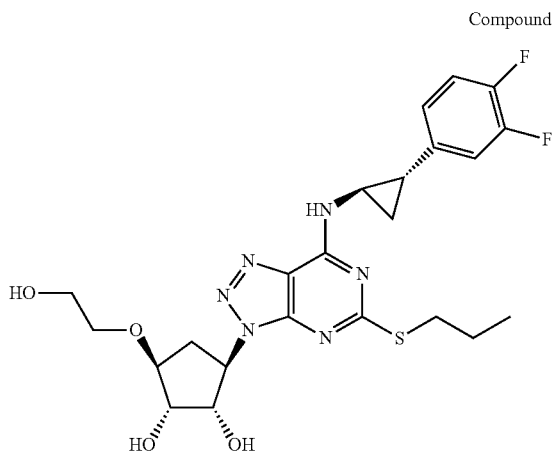

Compounds of formula (I) (see below) are useful in the preparation of Compound A and analogues thereof (see Example 3 of WO 01/92263).

In particular, the present invention provides a process for the preparation of a compound of formula (I):

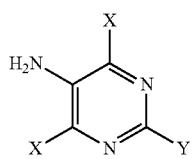

(I)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl; the process comprising hydrogenation in a suitable solvent of a nitro compound of formula (II)

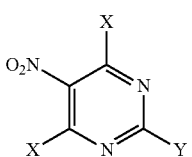

(II)

in the presence of a supported platinum catalyst according to the invention. In particular, the present compound of formula (II) is 4,6-dichloro-5-nitro-2-(propylthio)-pyrimidine (also named 4,6-dichloro-5-nitro-2-(propylsulfanyl)pyrimidine).

The modified catalysts according to the invention can be easily prepared and activated. It is therefore possible to prepare them fresh before use, thus ensuring maximum activity. The process of the invention may be used to hydrogenate both mononitro compounds and compounds having two or more nitro groups.

In a preferred embodiment the phosphorus compound is hypophosphorous acid ($H_3PO_2$) or a salt thereof, such as sodium or calcium hypophosphite, or a reaction product of said acid or salt. The term "reaction product" is to be understood to mean any product resulting from a chemical reaction of said acid or salt with the platinum catalyst or the molybdenum compound, with hydrogen, or with the aromatic or heteroaromatic nitro compound or its hydrogenation products.

In another preferred embodiment the molybdenum compound is an orthomolybdate or dimolybdate (i.e., a salt containing the $MoO_4^{2-}$ or $Mo_2O_7^{2-}$ anion) or a polymolybdate (e.g. a salt containing the $Mo_7O_{24}^{2-}$ anion), or a reaction product thereof. The term "reaction product" is to be understood to mean any product resulting from a chemical reaction of said molybdate with the platinum catalyst or the phosphorus compound, with hydrogen, or with the aromatic or heteroaromatic nitro compound or its hydrogenation products.

Especially preferred are orthomolybdates, in particular ammonium orthomolybdate (($NH_4)_2MoO_4$) or zinc orthomolybdate ($ZnMoO_4$).

The support (carrier) of the platinum catalyst may be any usual carrier including, but not limited to, alumina, silica and charcoal (activated carbon), charcoal being preferred.

The process of the invention is particularly suited to the hydrogenation of nitro compounds which are substituted with one or more substituents selected from the group consisting of halogen atoms and sulfur-containing groups, such as alkylthio (alkylsulfanyl, thioether) groups. Said substituents will not interfere with the reduction of the nitro group(s) by causing unwanted side reactions or catalyst poisoning.

More preferably the process is employed for the hydrogenation of heteraromatic nitro compounds such as nitropyridines or nitropyrimidines, the latter being particularly preferred.

A specifically preferred heteroaromatic nitro compound is 4,6-dichloro-5-nitro-2-(propylsulfanyl)pyrimidine which can be reduced to 5-amino-4,6-dichloro-2-(propylsulfanyl) pyrimidine.

The modified supported platinum catalyst containing molybdenum and a phosphorus compound, wherein the phosphorus has an oxidation state of less than +5, can be obtained by treating a supported platinum catalyst with an aqueous solution of hypophosphorous acid or a salt thereof and an orthomolybdate.

The molybdenum/platinum molar ratio is advantageously in the range of 1:1 to 100:1, preferably in the range of 1:1 to 10:1 and most preferably in the range of 1:1 to 5:1, while the phosphorus/molybdenum molar ratio is advantageously in the range of 1:1 to 100:1, preferably in the range of 1:1 to 10:1 and most preferably in the range of 1:1 to 5:1.

A suitable solvent for the hydrogenation of a compound of formula (II) is water, a $C_{1-6}$ aliphatic alcohol (such as ethanol and iso-propyl alcohol), an ether (for example a di($C_{1-6}$ alkyl) ether, such as diethylether or methyl tert-butyl ether; or a cyclic ether such as tetrahydrofuran), an ester (for example ethyl acetate) or a hydrocarbon solvent (such as an aromatic hydrocarbon, for example benzene, toluene or a xylene). Appropriate mixtures of such solvents may also be used.

In another aspect the hydrogenation of a compound of formula (II) is conducted at a temperature in the range 10 to 90° C., 20 to 70° C., 20 to 65° C., or 65° C.

In yet another aspect the hydrogenation of a compound of formula (II) is conducted at a pressure of 1 to 10 bar.

The following non-limiting examples will further illustrate the invention and its preferred embodiments. It should be understood that these examples are for illustrative purposes only and are not to be construed as limiting the invention in any manner.

EXAMPLE 1

Catalyst Preparation

To a slurry of 4.6 g of a commercial platinum on charcoal catalyst (5% Pt, Engelhard type 18, 40.5 weight % wet, lot #12410) in water (38 g), an aqueous solution of hypophosphorous acid (50%, 0.44 g, 3.4 mmol) was added and stirred for 15 minutes at 20° C. After this, ammonium orthomolybdate (($NH_4$)$_2$$MoO_4$, 0.27 g, 1.4 mmol; molar ratio $H_3PO_2$/($NH_4$)$_2$$MoO_4$=2.4:1; molar ratio ($NH_4$)$_2$$MoO_4$/Pt=2:1) was added to the slurry which was stirred vigorously over a period of 15 min and then transferred to the hydrogenation autoclave. The flask and the transfer line were flushed with tent-butyl methyl ether (31 g). The measured pH of the aqueous phase was 2.3 and the molybdenum content was 123 ppm.

EXAMPLE 2

5-Amino-4,6-dichloro-2-propylsulfanylpyrimidine tert-Butyl methyl ether (370 g) was placed under nitrogen in a 1 L stainless steel autoclave equipped with a temperature-controlled jacket, an Ekato InterMIG® stirrer, an internal temperature sensor and a dip pipe, and 4,6-dichloro-5-nitro-2-propylsulfanyl-pyrimidine (94.5 g, 0.35 mol) was added and dissolved at a stirring rate of 200 min$^{-1}$.

The catalyst suspension was prepared and transferred into the autoclave as described in the preceding example. The autoclave was sealed and the stirring rate was increased to 600 min$^{-1}$ while the autoclave was purged four times with nitrogen. Subsequently, hydrogen gas feed via the dip pipe at a constant flow rate ($p_{max}$=10 bar) as well as a heating-up ramp (45 K/h) from 20° C. to 65° C. were started in parallel, while stirring at 600 min$^{-1}$. The progress of the exothermic reaction was followed by recording the hydrogen uptake as well as the internal and jacket temperature curve. Upon completion of the hydrogen uptake (ca. 1.1 mol or 3 molar equivalents) after about 4 h, stirring of the reaction mixture was continued for an additional 3 hours at 65° C. After unloading the autoclave (the reactor was cooled down to 20° C., the hydrogen pressure was released and the reactor purged four times with nitrogen), the catalyst was filtered off. The autoclave as well as the filter cake (catalyst) were washed with tent-butyl methyl ether (185 g). The organic phases were combined and the water layer separated. An IPC-sample was taken to analyze the product mixture.

The conversion was found to be quantitative with no nitroso or hydroxylamine intermediate being detectable.
$^1$H NMR (CDCl$_3$, 400 MHz): δ 4.24 (br. s, 2H), 3.08 (t, J=7.2 Hz, 2H), 1.74 (sext., J=7.2 Hz, 2H), 1.02 (t, J=7.2 Hz, 3H).

EXAMPLE 3

Unmodified Pt/C Catalyst tert-Butyl methyl ether (370 g) was placed under nitrogen in a 1 L stainless steel autoclave equipped with a temperature-controlled jacket, an InterMIG® stirrer, an internal temperature sensor and a dip pipe. 4,6-Dichloro-5-nitro-2-propylsulfanylpyrimidine (94.5 g, 0.35 mol) was added and dissolved at a stirring rate of 200 min$^{-1}$. The autoclave was purged four times with nitrogen (stirring rate: 600 min$^{-1}$).

A slurry of the catalyst was prepared in a separate flask as follows: A commercial platinum on charcoal catalyst (4.6 g, 5% Pt, Engelhard type 18, 40.5 weight % wet, lot #12410; S/C=500:1) in water (38 g, 2.1 mol) was stirred for 15 min at 20° C. (the measured pH of the aqueous phase was 7.4). The resulting catalyst suspension was transferred into the autoclave and the flask and the transfer line were washed with tert-butyl methyl ether (31 g, 0.35 mol). The autoclave was then sealed and purged four times with nitrogen (stirring rate: 600 min$^{-1}$).

Subsequently, the dosage of the hydrogen gas via dip pipe with a constant flow rate ($p_{max}$=10 bar) as well as the heating-up ramp (45 K/h) to 65° C. was started in parallel, while stirring at 600 min$^{-1}$. The progress of the exothermic reaction was followed by measuring the hydrogen uptake as well as the internal and jacket temperature curve. After completion of the hydrogen uptake, the stirring (600 min$^{-1}$) of the reaction mixture was continued for an additional 3 h at 65° C.

After unloading the autoclave (the reactor was cooled down to 20° C., the H$_2$-pressure was released and the reactor purged four times with nitrogen), the catalyst was filtered off The autoclave as well as the filter cake (catalyst) was washed with tert-butyl methyl ether (185 g, 2.10 mol). The organic phases were combined and the water layer separated. An IPC-sample was taken to analyze the product mixture. Yield: 79%.

Various modifications of the invention, in addition to those described herein, will be apparent to those skilled in the art from the foregoing description. Such modifications are also intended to fall within the scope of the appended claims.

The invention claimed is:

1. A process for hydrogenating an aromatic or heteroaromatic nitro compound to the corresponding amine comprising:
   hydrogenating the aromatic or heteroaromatic nitro compound with a platinum catalyst, wherein the platinum catalyst comprises elemental platinum on a support, wherein the platinum catalyst has been modified with a molybdenum compound and a phosphorus compound, wherein the phosphorus has an oxidation state of less than +5.

2. The process of claim 1 wherein the phosphorus compound is hypophosphorous acid or a salt, or reaction product thereof.

3. The process of claim 1 wherein the molybdenum compound is an orthomolybdate or reaction product thereof.

4. The process of claim 3 wherein the molybdenum compound is ammonium orthomolybdate or zinc orthomolybdate, or a reaction product thereof.

5. The process of claim 1 wherein the support is charcoal.

6. The process of claim 1 wherein the catalyst has a molybdenum/platinum molar ratio of 1:1 to 100:1 and a phosphorus/molybdenum molar ratio of 1:1 to 100:1.

7. The process of claim 6 wherein the catalyst has a molybdenum/platinum molar ratio of 1:1 to 10:1 and a phosphorus/molybdenum molar ratio of 1:1 to 10:1.

8. The process of claim 1 wherein the aromatic or heteroaromatic nitro compound is substituted with one or more substituents chosen from halogen atoms and oxygen-containing or sulfur-containing groups.

9. The process of any claim 1 wherein the heteroaromatic nitro compound is a nitropyrimidine.

10. The process of claim 1 wherein the heteroaromatic nitro compound is a compound of formula (II)

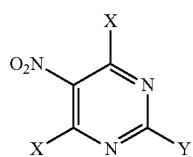

(II)

wherein X is halogen; Y is $ZR^1$; Z is oxygen or sulphur; and $R^1$ is $C_{1-6}$ alkyl, $C_{1-6}$ haloalkyl or $C_{3-7}$ cycloalkyl.

11. The process of claim 10 wherein the heteroaromatic nitro compound is 4,6-dichloro-5-nitro-2-(propylsulfanyl)pyrimidine.

12. A modified supported platinum catalyst comprising molybdenum and a phosphorus compound, wherein the phosphorus has an oxidation state of less than +5, obtainable by treating a supported platinum catalyst with an aqueous solution of hypophosphorous acid or a salt thereof and an orthomolybdate in a molybdenum/platinum molar ratio of 1:1 to 100:1 and a phosphorus/molybdenum molar ratio of 1:1 to 100:1.

13. The modified supported platinum catalyst of claim 12 wherein the molybdenum/platinum molar ratio is from 1:1 to 10:1 and the phosphorus/molybdenum molar ratio is from 1:1 to 10:1.

14. The modified supported platinum catalyst of claim 12 wherein the orthomolybdate is selected from ammonium orthomolybdate and zinc orthomolybdate.

* * * * *